United States Patent [19]

Romanowski

[11] Patent Number: 4,667,672

[45] Date of Patent: May 26, 1987

[54] PRESSURE CUFF

[76] Inventor: Richard Romanowski, Axel Danielssons väg 49, S-214 74 Malmö, Sweden

[21] Appl. No.: 758,668

[22] PCT Filed: Oct. 25, 1984

[86] PCT No.: PCT SE 84/00358

§ 371 Date: Jul. 3, 1985

§ 102(e) Date: Jul. 3, 1985

[87] PCT Pub. No.: WO 85/01868

PCT Pub. Date: May 9, 1985

[30] Foreign Application Priority Data

Oct. 25, 1983 [SE] Sweden ............................... 8305855

[51] Int. Cl.$^4$ .......................... A61B 17/12; A61B 5/02
[52] U.S. Cl. ..................................... 128/327; 128/686; 128/685; 128/DIG. 20
[58] Field of Search ............... 128/685, 686, 327, 677, 128/346, 325, DIG. 25, DIG. 20, 60

[56] References Cited

U.S. PATENT DOCUMENTS

| | | | |
|---|---|---|---|
| 2,781,041 | 2/1957 | Weinberg | 128/60 |
| 2,943,859 | 7/1960 | Koski et al. | 128/327 |
| 3,454,010 | 7/1969 | Lilligren et al. | 128/327 |
| 3,862,629 | 1/1975 | Rotta | 128/DIG. 20 |
| 4,067,075 | 1/1978 | Leathers et al. | 128/DIG. 20 |
| 4,522,197 | 6/1985 | Hasegawa | 128/DIG. 20 |

FOREIGN PATENT DOCUMENTS 1491215 6/1969 Fed. Rep. of Germany.
381986 1/1976 Sweden.

Primary Examiner—Richard J. Apley
Assistant Examiner—H. Macey
Attorney, Agent, or Firm—Roberts, Spiecens & Cohen

[57] ABSTRACT

A substantially tubular cuff adapted to enclose a part of the body and apply pressure thereto, in order to achieve and maintain, in a circumferential region of the enclosed part of the body, a fluid-and gas-depleted field and/or in order to comprise a support and/or pressure bandage. The cuff includes substantially annular chambers (4) distributed one after the other in the axial direction of the cuff and adjacent to each other, whose walls (41) consist primarily of flexible and/or elastic materials. The chambers are enclosed by a common outer circumferential pressure cell (3) which extends in the axial direction of the cuff and which is provided with connection devices (12,13) in order to pressurize the cell (3) by a pressure medium from an external pressure source (14). The pressure cell has a wall (5) which faces the chambers (4) and is connected or integral with valve devices (6) to shut or open communication devices for passage of a pressure medium between adjacent chambers. When using the cuff the pressure cell (3) is given an increased internal pressure which controls the opening of the valve devices (6) when the chambers (4) are supplied with pressure medium.

7 Claims, 9 Drawing Figures

PRESSURE CUFF

FIELD OF THE INVENTION

The present invention relates to a substantially tubular equipment (cuff) adapted in order to enclose a part of the body and thus apply a pressure thereto, in order to achieve and maintain, in a circumferential region of the enclosed part of the body, a fluid- and gas-depleted field, such as a blood-evacuated field, and/or in order to comprise a support- and/or pressure bandage and/or to fix the part of the body mechanically.

BACKGROUND

Arrangements in accordance with the above are generally designated blood evacuation and blood pressure cuffs and are used, e.g., in operations. Such cuffs are important aids especially in orthopaedics, and hand, nerve, vascular, and plastic surgery. These cuffs are also employed in such applications as support and pressure bandages, e.g., in transporting casualties.

The use of blood evacuation and blood pressure cuffs sometimes results, however, in injuries to blood vessels and nerves due to the mechanical pressure which the cuff exerts on the underlying body tissue. The pressure against the body tissue causes a displacement of tissue from compressed to non-compressed tissue portions, which results in mechanical tissue deformation which is maximal in regions where the pressure gradient is at its greatest. When injuries occur, these are a rule maximal in both musculature and nerve tissues in the immediate vicinity of regions with large pressure gradients. Hitherto known cuffs achieve an uneven distribution of pressure on the body tissue in both the longitudinal direction of the cuff and its circumferential direction, which increases the risk of injuries to the body tissue. In order to reduce the risk of injury, it is thus necessary in use to keep the cuff pressure as low as possible. Especially in the vicinity of the edges of the cuff the pressure differences are large, and thus increase the risk of injury with an uneven pressure distribution in the circumferential direction of the cuff.

A further disadvantage of hitherto known and used cuffs is that in use they strive towards centring the enclosed part of the body in the cuff. This comprises a complication since the enclosed regions have an irregular shape, and a centring may imply undesirable displacements in the enclosed part of the body.

Patent publication No. SE 7400412-8 reveals a blood evacuation cuff which consists of a number of transverse, series-connected, inflatable sections which are disposed on the inside of a stable-shaped cloth which can be shaped into a slightly conical cylinder in that the end regions of the cloth are joined by means of a zip fastener. A successive filling of the sections and thus a corresponding increase in the pressure against the enclosed part of the body can take place by means of valves of a rather complicated structure, connection devices for compressed air, and regulating devices. The valves between the different sections give rise to a certain pressure drop, for which reason the pressure in the last section is considerably lower than in the first in its filled state. For this reason the pressure in the first section must be set to an unnecessarily high value, if the pressure in the last section is to be sufficient. This is a disadvantage. When the cuff is applied to a part of the body with variations in shape and cross-section, local differences in the pressure on the part of the body also occur, since the internal shape of the cuff is defined primarily by the shape of the cloth. In the longitudinal direction of the cuff there runs along the zip fastener (the seam) a zone which lacks inflated sections, and thus the seam causes variations in the pressure on the underlying part of the body. Such an asymmetry with regard to the pressure forces has solely a harmful effect on the part of the body in question.

Patent publication No. SE 7714599-3 reveals a blood evacuation cuff which consists of a number of sections similar to those described above,. In this cuff use is made of a connection tube to each section as well as distribution equipment, which completes the design. This cuff too has the disadvantage of an uneven pressure distribution in application to a part of the body which has a varying shape and cross-section.

SUMMARY OF THE INVENTION

An object of the present invention is to provide a cuff equipment, where the disadvantages of the known technique are eliminated and which thereby is as gentle as possible on the patient.

The invention is based on a cuff equipment which in tubular in application, the equipment including substantially annular chambers, distributed one after the other in the axial direction of the cuff and adjacent to each other, and the walls of the chambers consisting substantially of flexible and/or elastic materials.

The specific feature of this invention is that the annular chambers are enclosed by a common outer circumferential substantially slotlike pressure cell which extends in the axial direction of the equipment and which is provided with connection devices in order to pressurise the cell by means of a pressure medium from an external pressure source. At least the delimiting wall which the pressure cell faces towards the chambers includes flexible and/or elastic materials. The delimiting wall is connected to valve devices for acting on the devices or forms part of valve devices, the valve devices being disposed in order to shut or open communication devices for passage of a pressure medium between adjacent chambers. At least one of those chambers which are located outermost in the row of chambers is provided with connection devices in order to pressurise said chambers from an external pressure source.

In a preferred embodiment of the invention the chambers, which are substantially circumferential when applying the cuff, are also disposed with sub-chambers, which by means of valve devices open passages to adjacent sub-chambers.

BRIEF DESCRIPTION OF THE DRAWING

The invention is described in greater detail in conjunction with a number of figures, wherein.

DETAILED DESCRIPTION OF PREFERRED EMBODIMENTS

Figure 1:
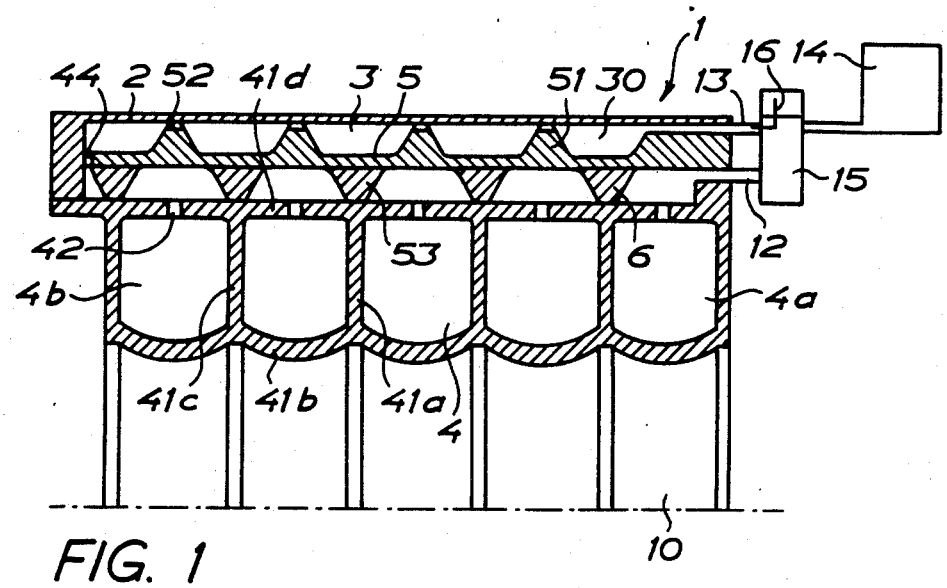
FIG. 1 shows a longitudinal section through a principal embodiment of the cuff.

FIG. 1 shows in a longitudinal section a principal embodiment of a tubular cuff equipment 1 (hereinafter the designation cuff is used for this) which includes an outer layer 2, a circumferential pressure cell 3 disposed behind this which extends primarily through the entire length of the cuff and a number of torus-shaped enclosures or chambers 4 with at least partially flexible walls 41a–d, which chambers are disposed one after the other behind the pressure cell in the longitudinal direction of the cuff. The chambers 4 each have at least one aperture 42 for the supplying or evacuation of a pressure medium such as air or water. Adjacently located chambers 4 are joined via their apertures 42 by means of valve devices 6 for the passage of a pressure medium.

The pressure cell 3 is isolated from the chambers 4 by means of a separating wall 5 which is joined to the outer layer 2 by means of spaces or fixing devices 51 disposed in the circumferential direction of the cuff and at a distance from one another. Between the fixing devices there are thus formed cavities 30 which form part of the pressure cell 3 and which are joined to each other by means of ducts 52 disposed in the fixing devices 51 or between them. The outer layer 2 and the wall 5 thereby assume substantially fixed positions relative to each other in the case of both a pressurised and non-pressurized pressure cell 3. Between the wall 5 and the walls 41d which the chambers 4 present to the outer layer, there are also disposed fixing devices 53 placed in the circumferential direction of the cuff at a distance from each other. In certain applications the fixing devices 53 also comprise the valve devices 6 as shown in the figure. The aforementioned fixing devices keep the wall 41d opposite the outer layer 2 and thus the chambers 4 fixed to the wall 5, and thus also the wall and the chambers in a substantially fixed position relative to the outer layer 2. In the embodiment shown the aforementioned fixing devices 53 also comprise the valve devices 6. This is achieved in that the fixing devices along relative short sections located in the circumferential direction are not attached to the outwards-facing walls 41d of the chambers 4, in order to make it possible for the fixing devices to be detached somewhat from the walls 41d, thereby allowing passage of a pressure medium between the fixing devices and the outer walls 41d.

The cuff is disposed with connection devices 12, 13 in an edge portion 10 for the supplying of a pressure medium to the pressure cell 3 and the chambers 4. These devices connect an outer chamber 4a located in the edge portion and the pressure cell 3, respectively, to a reservoir 14 via pressure regulation devices 15 and a valve 16 which is disposed to assume positions in which the connection devices individually and on separate occasions are connected to the reservoir, simultaneously connected thereto and/or connected to each other. Furthermore, the embodiment shown includes a duct 44, which, in the vicinity of the outermost chamber 4b in the end region which is opposite the end region located in the vicinity of the inlet ducts 12,13, connects the region between the chambers 4 and the wall 5 to the pressure cell 3.

Figure 2:
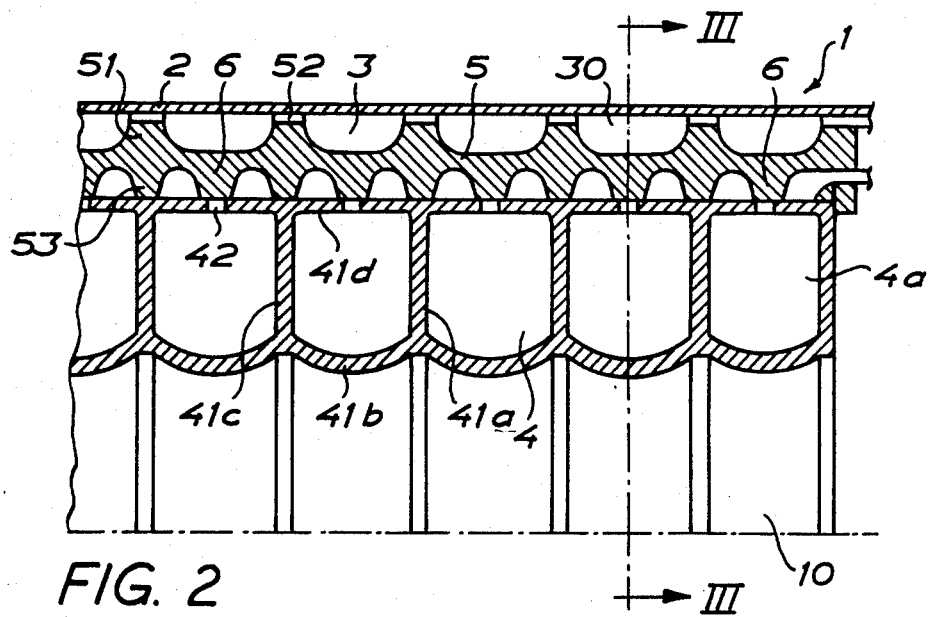
FIG. 2 shows the longitudinal section II—II in FIG. 3.
Figure 3:
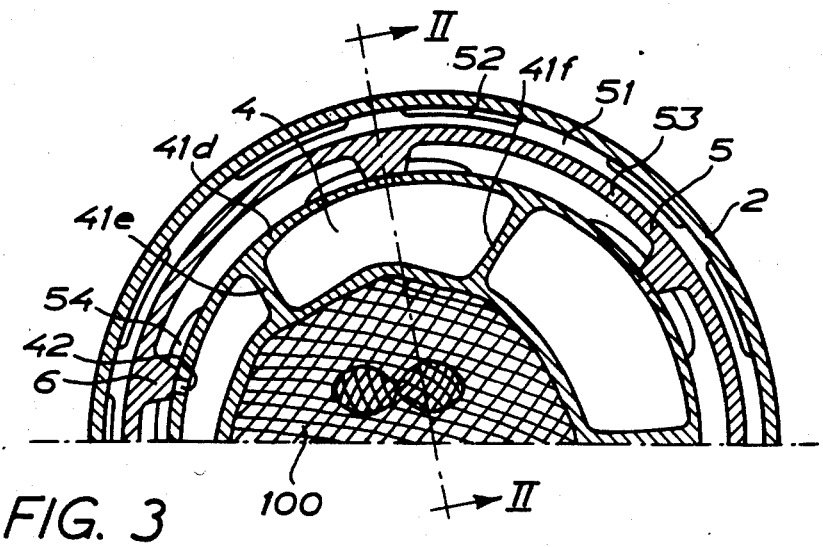
FIG. 3 shows the cross-section III—III in FIG. 2.

FIGS. 2 and 3 show an embodiment of the cuff where the valve devices 6 are disposed in the immediate vicinity of the apertures 42 of the chambers. The fixing devices 51 for the connection of the wall 5 to the outer layer 2 and the fixing devices 53 for the attachment of the chambers 4 to the wall 5 are in the embodiment shown disposed pairwise in planes which for every pair are substantially perpendicular to the axis of the cuff. In order to allow passage of a pressure medium between chambers which are located adjacent to each other in the longitudinal direction of the cuff, the fixing devices 53 are provided with ducts 54. The figure also indicates how a part of a body 100 is enclosed by the pressurized cuff.

In the use of the cuff the latter is applied around the part of the body in question, after which a pressure medium is supplied to the pressure cell 3 so that an overpressure adapted to the treatment in question is achieved therein. Pressure medium is subsequently supplied to the outer chamber 4a in the edge portion 10 which successively receives an increasing pressure until the pressure in the pressure cell 3 is no longer able to keep the valve device 6 in a closed position. When the valve device 6 opens, filling of the subsequent chamber 4 with pressure medium is initiated, which filling proceeds until a following valve device 6 between the now filled and pressurized chamber 4 and the subsequent chamber is opened. As a consequence there is achieved the required effect of a gradual build-up of the pressure against the part of the body, and a gradual expansion of the region which is being pressurized. Prior to the removal of the cuff the connection devices 12,13 are opened to their surroundings so that pressure medium is removed from the pressure cell 3 and the chambers 4, by which means the cuff regains its flexible shape and can be taken off the part of the body.

In the case of the embodiment shown in the FIGS. 2 and 3 there also takes place a gradual build-up of the abutment pressure against the part of the body in the circumferential direction of the cuff. Once the pressure cell 3 has been pressurized, all sub-chambers of a first circular chamber 4a are filled with pressure medium. When all sub-chambers therein due to the pressure in the pressure cell attain a final pressure determined by the pressure in the pressure cell 3, the connection 42 for pressure medium to each sub-chamber is closed, which takes place by means of the valve 6 and the subsequent circumferential chamber 4, it too composed of a number of sub-chambers distributed in the circumferential direction, and is pressurized in accordance with the forementioned procedure. Once all sub-chambers in the circumferential chamber in question have received their final pressure, the procedure described continues in the next circumferential chamber 4. The embodiment shown in FIGS. 2 and 3 thus divides the pressurized region also in the circumferential direction into a number of sub-regions, which means that once each sub-chamber has attained its final pressure and its specific and individual volume associated therewith, it no longer strives to expand any further. By this means the effect is thus achieved that the pressurization of the part of the body takes place without the cuff simultaneously having any tendency to attempt to center the part of the body therein. The duct 44 to the pressure cell 3 equalizes the pressure between the chambers 4 and the wall 5. In certain applications the increase in pressure which thus occurs in the pressure cell 3 is used in order to actuate the pressure regulation device 15 so as to shut off the cuff to any further supply of pressure medium. In other applications a manual setting of the pressure regulation device 15 is undertaken for this purpose.

Figure 4:
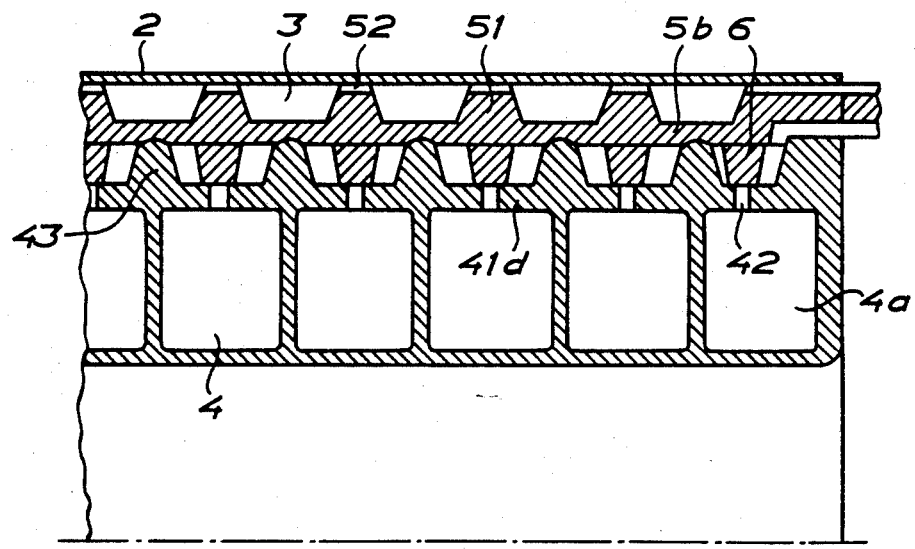
FIGS. 4,a,b and 5 show in their upper portions longitudinal sections through alternative embodiments of the cuff and in their lower portions, respectively, devices seen from the side.
Figure 4A:
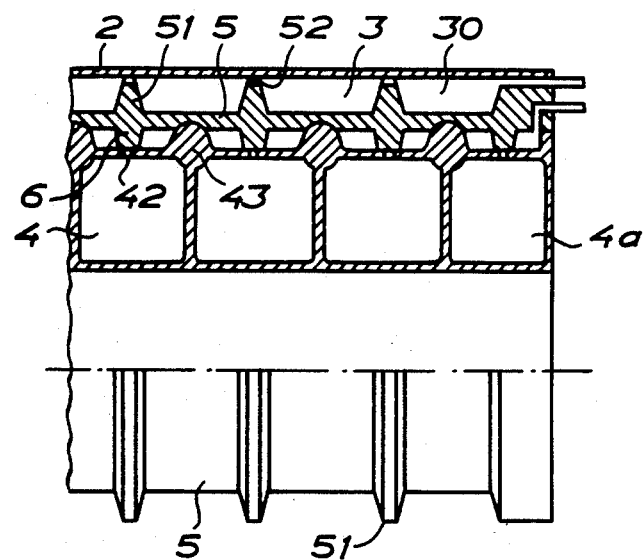
Figure 4B:
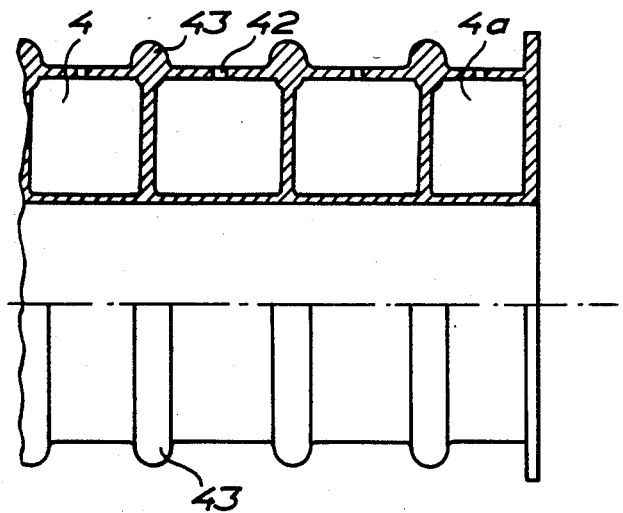

FIGS. 4, 4a,b show an alternative embodiment of the cuff where the chambers 4 have their wall 41d facing the outer layer 2 provided with fixing devices 43 which fix the chambers 4 relative to the wall 5b which delimits the pressure cell 3 form the center of the cuff. In FIG. 4a, in its lower section, the outer layer 2 is removed, and in FIG. 4b there is shown in the upper part a section through the row of chambers and in its lower part the row of chambers from the side. The latter figure shows especially how the parts of the chambers located immediately next to the outer layer are stabilized mechanically with the aid of the circumferential fixing devices 43 and adjacent thickened portions in the walls of the chambers.

In the embodiment shown in FIGS. 4,4a,b the valve device 6 and the fixing devices 51 are furthermore located in common planes, substantially perpendicular to the axis of the cuff. In one or more regions between the fixing devices 43 and the wall 5b the fixing device 43 is not attached to the wall 5b in order to form therewith valve devices, whose opening is controlled by the pressure difference between the pressure cell 3 and the pressures in each chamber 4. In other embodiments there are disposed ducts in the vicinity of the fixing devices 43 without any valve action for passage of a pressure medium. The function and operating mode of the cuff correspond in principle to that which has already been described in conjunction with FIGS. 1-3.

Figure 5:
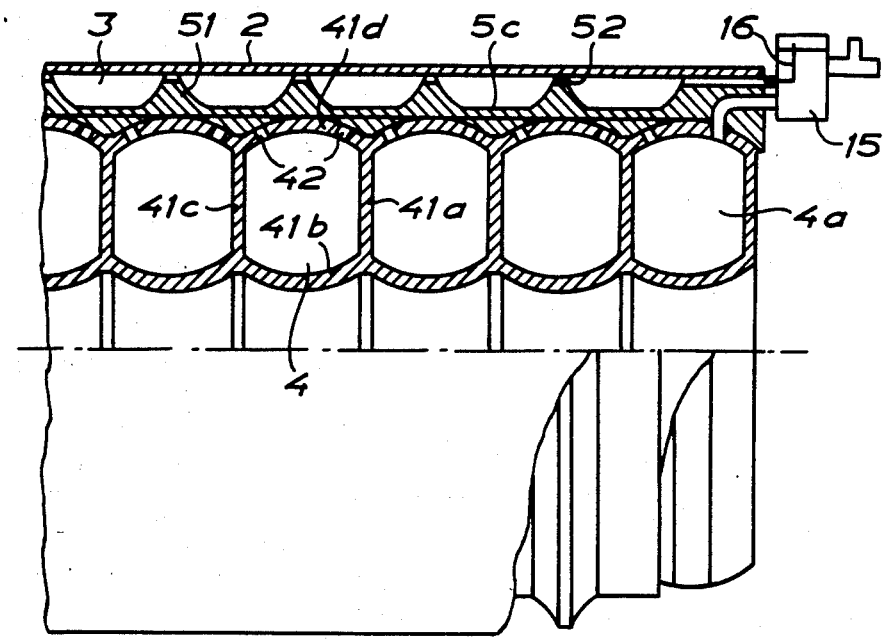

FIG. 5 shows a further embodiment of the invention where every chamber 4 is disposed with apertures 42, located in the upper wall 41d and in the vicinity of the delimiting walls 41a and 41c. The wall 5c of the pressure cell which faces the center of the cuff is, in a preferred embodiment, fixed to the chambers 4 in circumferential regions separated from each other and located in the vicinity of the dividing walls between the chambers. Each such circumferential region contains portions in which the material in the wall 5c is not fixed to the material in the walls 41d of the chambers 4. In these regions there are thus formed ducts between the adjacent apertures 42 of the adjacently located chambers 4, when the pressure in one of the chambers is capable of counteracting the pressure from the pressure cell 3 in addition to the elastic forces in the material. Also in this embodiment of the cuff the mode of operation is in agreement with what has been previously described in conjunction with FIGS. 1-3.

Figure 6A:
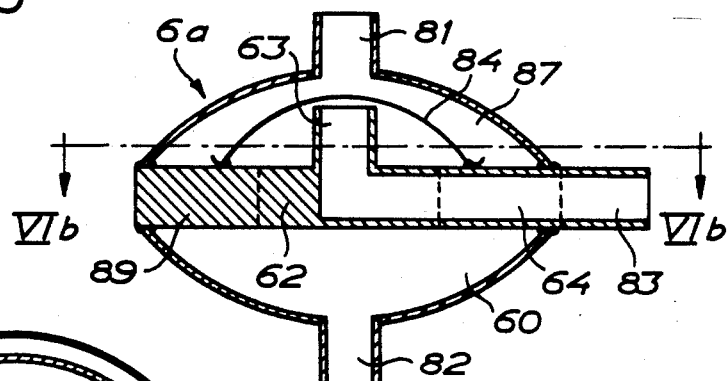
FIGS. 6a,6b show an alternative embodiment of a valve device.
Figure 6B:
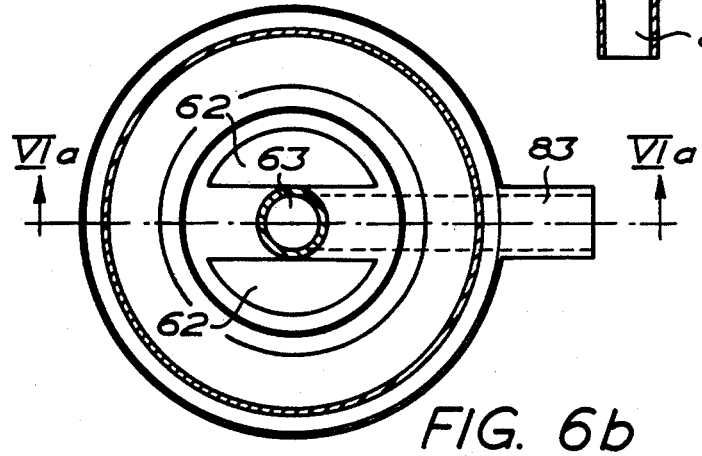

FIGS. 6a and 6b shows a principal version of an alternative embodiment of the valve 6a. The valve includes a space 87 and a closed space 60 which are separated from each other by means of a dividing wall 89. The dividing wall includes a duct 64 whose end 83 opens outside the valve and whose other end 63 opens into the space 87. A diaphragm 84 is fixed sealingly to the dividing wall 89 and encloses in addition the other end 63 of the duct 64. Behind the diaphragm there are ducts 62 disposed in the dividing wall 89, which ducts open into the closed space 60. A connection 81 joins the space 87 to its surroundings. The closed space 60 is also disposed with a connection 82 which joins the space to its surroundings.

When valves in accordance with FIGS. 6a and 6b are used in a cuff arrangement in accordance with the invention, the connection 81 for each valve is coupled to the pressure cell 3, the connection 82 to a chamber 4, and the one end 83 of the duct 64 to a chamber 4 which seen in the direction of filling is located prior to the chamber to which the connection 82 was coupled. When a pressure medium is supplied to the pressure cell 3, the space 87 in each valve is supplied with a pressure medium which causes the diaphragm 84 to seal off the end 83 of the duct 64. When a pressure medium is then supplied to the valve, the diaphragm 84 lifts away from the aperture of the end 63 of the duct, when a sufficiently high pressure has been reached in the duct 64, and the pressure medium passes through the duct 62 to the closed space 60 and from there via the connection 82 to the subsequent chamber 4. By adapting the elasticity of the diaphragm 84, the overpressure in the duct 64 which is required for the valve to open is regulated. When the chamber 4 to which the end 83 is coupled has reached a sufficiently large internal pressure, the passage to an adjacent chamber is opened, in that the valve connected between the chambers is opened by means of a procedure which corresponds to that which has been described heretofore.

The invention has been described in the preceding description in a number of embodiments which show varying constructions above all of the dividing wall which delimits the pressure cell 3 in a direction towards the center of the cuff. The embodiments of the dividing wall 5 shown only illustrate the versatility of the invention and show the inventive concept can be easily realized in a large number of embodiments. The embodiments of the valve arrangements shown should also be viewed as exemplifications of valve arrangements which can be used within the scope of the invention.

The above detailed description has referred solely to a limited number of embodiments of the invention, but it will be readily understood by a person skilled in the art that the invention accommodates a large number of embodiments within the scope of the claims hereinafter.

What is claimed is:

1. A tubular cuff apparatus for achieving and maintaining fluid- and gas-depleted regions in parts of the body of a patient comprising a plurality of substantially annular chambers extending around an axis, said chambers being distributed one after the other adjacent to one another along said axis, walls separating said chambers and constituted by elastic material, a common outer circumferential, substantially slot-like pressure cell enclosing said annular chambers, said pressure cell extending along said axis and including connection means for pressurizing said cell by a pressure medium from an external pressure source, said pressure cell including a separating wall facing said chambers and constituted of elastic material, and valve means connected to said separating wall for selectively opening or closing communication between adjacent chambers for passage of a pressure medium between adjacent chambers, the outermost one of said chambers including connection means for pressurizing said outermost chamber from an external pressure source.

2. Apparatus as claimed in claim 1 wherein said pressure cell includes an outer wall and spacer means on said outer wall for maintaining a specific distance between said outer wall and said separating wall.

3. Apparatus as claimed in claim 2 wherein said spacer means comprises spacer elements which divide said pressure cell into a plurality of intercommunicating cavities.

4. Apparatus as claimed in claim 1 wherein said valve means comprises a plurality of valve devices each associated with a respective chamber, the valve device associated with the end chamber most remote from said connection means selectively providing communication between said end chamber and said pressure cell via a communication means therebetween.

5. Apparatus as claimed in claim 1 wherein each annular chamber includes wall dividing each chamber into subchambers distributed one after the other in the circumferential direction of said chamber, said valve means including valve devices arranged around each annular chamber to selectively close communication between said subchambers at an internal pressure in each subchamber related to the pressure in said pressure cell.

6. Apparatus as claimed in claim 1 comprising duct means located in the vicinity of the end chamber most remote from said connection means for connecting said end chamber to said pressure cell.

7. Apparatus as claimed in claim 6 wherein said duct means comprises a duct in said separating wall.

* * * * *